United States Patent
Romare

[19]

[11] Patent Number: 6,162,204
[45] Date of Patent: Dec. 19, 2000

[54] ABSORBENT ARTICLE WITH IMPROVED FORMING ABILITY

[75] Inventor: Anette Romare, Möndal, Sweden

[73] Assignee: SCA Hygiene Products AB, Gothenburg, Sweden

[21] Appl. No.: 09/192,942

[22] Filed: Nov. 16, 1998

[30] Foreign Application Priority Data

Nov. 17, 1997 [SE] Sweden ................................ 97/04191

[51] Int. Cl.⁷ .................................................. A61F 13/15
[52] U.S. Cl. ........................... 604/385.01; 604/385.22; 604/385.23
[58] Field of Search ...................... 604/385.1, 385.2–387, 604/385.01, 385.03

[56] References Cited

U.S. PATENT DOCUMENTS

| | | | |
|---|---|---|---|
| 3,570,493 | 3/1971 | Olsson . | |
| 4,891,258 | 1/1990 | Farenkrug | 428/138 |
| 4,892,536 | 1/1990 | DesMarais et al. | 604/385.2 |
| 4,911,701 | 3/1990 | Mavinkurve | 604/385.2 |
| 5,007,906 | 4/1991 | Osborn, III et al. | 604/385.1 |
| 5,171,302 | 12/1992 | Buell | 604/385.1 |
| 5,197,959 | 3/1993 | Buell | 604/385.1 |
| 5,300,055 | 4/1994 | Buell | 604/385.1 |
| 5,324,278 | 6/1994 | Visscher et al. | 604/385.1 |
| 5,346,486 | 9/1994 | Osborn, III et al. | 604/385.1 |
| 5,354,400 | 10/1994 | Lavash et al. | 604/385.1 |
| 5,389,094 | 2/1995 | Lavash et al. | 604/385.1 |
| 5,558,656 | 9/1996 | Bergman | 604/385.1 |
| 5,591,150 | 1/1997 | Olsen et al. | 604/385.1 |
| 5,611,790 | 3/1997 | Osborn, III et al. | 604/385.1 |
| 5,702,378 | 12/1997 | Widlund et al. . | |
| 5,993,431 | 11/1999 | McFall et al. | 604/385.2 |

FOREIGN PATENT DOCUMENTS

| | | |
|---|---|---|
| 298348 | 1/1989 | European Pat. Off. . |
| 335253 | 10/1989 | European Pat. Off. . |
| 419434 | 3/1991 | European Pat. Off. . |
| 442223 | 8/1991 | European Pat. Off. . |
| 2296191 | 6/1996 | United Kingdom . |
| 88/04547 | 6/1988 | WIPO . |

*Primary Examiner*—John G. Weiss
*Assistant Examiner*—Caiu Mager
*Attorney, Agent, or Firm*—Young & Thompson

[57] ABSTRACT

An absorbent article with a longitudinal direction and a transverse direction and displaying a crotch part (7) and two end parts (5, 6) and comprising a liquid-permeable cover layer (2) intended to face towards a user during use, a liquid-impermeable cover layer (3) intended to face away from the user during use and an absorbent body (13) enclosed between the two cover layers (2, 3). The two cover layers (2, 3) have differing extensibility in the transverse direction of the article. A forming element (16; 514; 814), which is rigid in the transverse direction and which extends in the transverse direction of the article at least in the crotch part (7) is permanently attached to at least one component in the article, whereby compression of the article in the transverse direction will force the forming element (16; 514; 814) to curve in a direction towards the most extensible cover layer (2; 503; 802, 803).

12 Claims, 4 Drawing Sheets

ABSORBENT ARTICLE WITH IMPROVED FORMING ABILITY

TECHNICAL FIELD

The invention concerns an absorbent article with a longitudinal direction and a transverse direction and displaying a crotch part and two end parts and comprising a liquid-permeable cover layer intended to face towards a user during use, a liquid-impermeable cover layer intended to face away from the user during use and also an absorbent body enclosed between the two cover layers.

PRIOR ART

An absorbent article such as a sanitary napkin or an incontinence protector is designed to be accommodated in the crotch part of a pair of underpants. The article is usually provided with an adhesive member in the form of self-adhesive glue for attaching the article to the underpants. One demand that is made on articles of this type is that they should be able to be concealed by normal clothing. It is therefore important for the article to be as small and discrete as possible. This means that such an article, compared with, for example, diapers, has a relatively small width. When the article is in use, the width is further reduced due to the article being compressed between the legs of the user. In this way, the surface of the article that is available to receive liquids is reduced, which means that there is a considerable risk of body fluid running out beyond the side edges of the article.

The liquid-acquisition capacity of the absorbent article can be further reduced by the side edges of the article being folded in over the liquid-permeable surface of the article during use. As the underside of the article is usually covered with a liquid barrier material, the liquid-permeable surface will then be reduced.

A further problem in connection with absorbent articles of this type is that they are deformed so greatly during use that cracks and folds are formed in the absorbent material. Such folds and cracks act as channels which lead liquid out of the article. Furthermore, they affect the spread of liquid in the absorbent article in an uncontrolled manner with the result that the article can be perceived as lumpy and uncomfortable.

Absorbent articles such as incontinence protectors and sanitary napkins are usually constructed of an absorbent body which is enclosed in a cover comprising a liquid-permeable surface layer. It is not unusual for the liquid-permeable surface layer also to be wrinkled in a manner which has a negative effect on the leakage security and comfort of the article.

A number of different solutions have been suggested in order to overcome the problems of leakage and lack of comfort which undesired and uncontrolled deformation of an absorbent article can give rise to.

For example, the absorbent article can be provided with some type of insert integrated into the article, which insert counteracts the compressing force to which the article is subjected during use. The insert can be formed so that the article is given a certain predetermined form during use. Such inserts are described in, for example, EP-A-0,335,253, EP-A-0,298,348 and U.S. Pat. No. 3,570,493. However, a disadvantage of the known inserts is that they require extra manufacturing steps and moreover raise the cost of materials for the absorbent article. As an insert must be resistant to moisture in order to avoid being destroyed by body fluids that are absorbed by the article and is therefore usually formed of a non-absorbent liquid-impermeable material, the presence of such an insert has a negative effect on the ability of the article to receive and absorb body fluid.

Other methods of increasing the leakage security of an absorbent article are by forming the article, for example with the aid of an elastic member. Such an example is given in EP-A-0,091,412, which publication describes a sanitary napkin displaying elastic members arranged along the side edges. The elastic members pull the material together in the side edges of the sanitary napkin, whereby the material in the side edges forms raised edge barriers while the napkin is curved in the longitudinal direction so that a liquid-receiving bowl shape is formed between the edge barriers.

Another method of forming an absorbent article by means of elastic members is shown in WO 88/04547. This publication concerns a sanitary napkin which is given a soft, resilient hump on the surface that is intended to face the user during use. The hump is formed by arranging elastic members in the transverse direction of the napkin on the underside of the napkin, i.e. adjacent to the napkin's liquid-impermeable barrier layer.

Furthermore, it is known to improve leakage security and user comfort by using other methods to form absorbent articles with bowls, raised portions, edge barriers, or the like. For example, it is possible to form humps, ridges, or the like by accumulation of the absorbent material. Another way of creating a raised portion on an absorbent article by curving the article and locking the side edges at a predetermined mutual distance is described in EP-A-0 419 434.

However, all such previously known three-dimensionally formed absorbent articles have the great disadvantage that the three-dimensional form presents difficulties both during manufacture of the absorbent articles and when they are to be packaged. For example, the majority of the known three-dimensionally formed absorbent articles are impossible to fold together into a convenient packaging format without a negative effect on both form and function. Thus, there remains a great demand for an absorbent article with high leakage security, which article is simple to produce, requires a minimum of components and can be packed flat or folded together.

BRIEF DESCRIPTION OF THE INVENTION

By means of the present invention, however, an absorbent article of the type described in the introduction has been brought about, with which the disadvantages of previously known such articles have been almost completely eliminated.

An article produced in accordance with the invention is principally characterised in that the two cover layers have differing extensibility in the transverse direction of the article, and also in that a forming element which is rigid in the transverse direction and which extends in the transverse direction of the article at least in the crotch part is permanently attached to at least one component in the article, whereby compression of the article in the transverse direction will force the forming element to curve in a direction towards the most extensible cover layer.

An absorbent article with a liquid-permeable cover layer which displays greater extensibility in the transverse direction of the article than the liquid-impermeable cover layer is affected by the compression of the article in the transverse direction which arises during use so that the forming element is made to curve in a direction towards the liquid-permeable cover layer. In this way, the article displays during use a raised portion facing towards the user. Due to the fact that the relatively less extensible liquid-impermeable cover layer counteracts the curving of the article into a bowl form facing towards the user, the curving will occur in the direction which presents the least resistance, namely towards the liquid-permeable cover layer. The opposite relationship applies in the case of an absorbent article in which the liquid-impermeable cover layer displays greater extensibility in the transverse direction of the article than the liquid-permeable cover layer. Accordingly, compression of the article in the transverse direction causes the forming element to bend in a direction towards the liquid-impermeable cover layer whereby the article during use displays a bowl shape facing towards the user.

The forming element can be constituted of a fibre layer with a density of at least 0.2–1–0 g/cm$^3$. Examples of such fibre materials are given in WO 94/10953 and WO 94/10956. When fibre layers are used as forming elements, they can have varying absorbency or be completely nonabsorbent.

Alternatively, the forming element can be constituted by a rigid plastic layer, foamed plastic layer, metal layer, or the like. However, it is essential that the forming element is not so rigid that it is not bent into the desired arc shape by the forces which normally arise during use of absorbent articles intended to be worn between the thighs of a user. Accordingly, the forming element shall be able to be curved, without discomfort to the user, by the pressure forces which act in the transverse direction of the article due to the article being compressed between the thighs of the user during use. The forming element should not be folded, broken or loosened to any great degree by the forces which affect the forming element during use. These forces are, apart from the compressing forces between the thighs, a counter force from the genital area of the user and a supporting force from the underpants of the user. Moreover, when the user sits down on a surface, the article is subjected to pressure forces from the surface.

The most extensible cover layer can be elastically extensible. After stretching, an elastically extensible material strives to at least partly return to its unstretched condition. The less extensible cover layer is preferably non-extensible, i.e. substantially unaffected when it is subjected to the tensile forces that can arise during use of the article.

According to the invention, the forming element can be attached to one or several of the components in the article, such as the liquid-impermeable cover layer, the liquid-permeable cover layer or the absorbent body. The seal can be made over a large or small part of abutting surfaces of the forming element and the other components of the article.

If the forming element is arranged so at there are one or several absorbent components between the liquid-impermeable cover layer and the forming element, it is advantageous if the forming element is liquid-permeable. Alternatively, the forming element can extend to such a small degree in the longitudinal direction of the article that its negative effect on the flow of liquid to the components lying beneath is negligable.

BRIEF DESCRIPTION OF THE FIGURES

The invention will be described in more detail below with reference to the embodiments which are shown on the accompanying drawings, in which.

DESCRIPTION OF EMBODIMENTS

Figure 1:
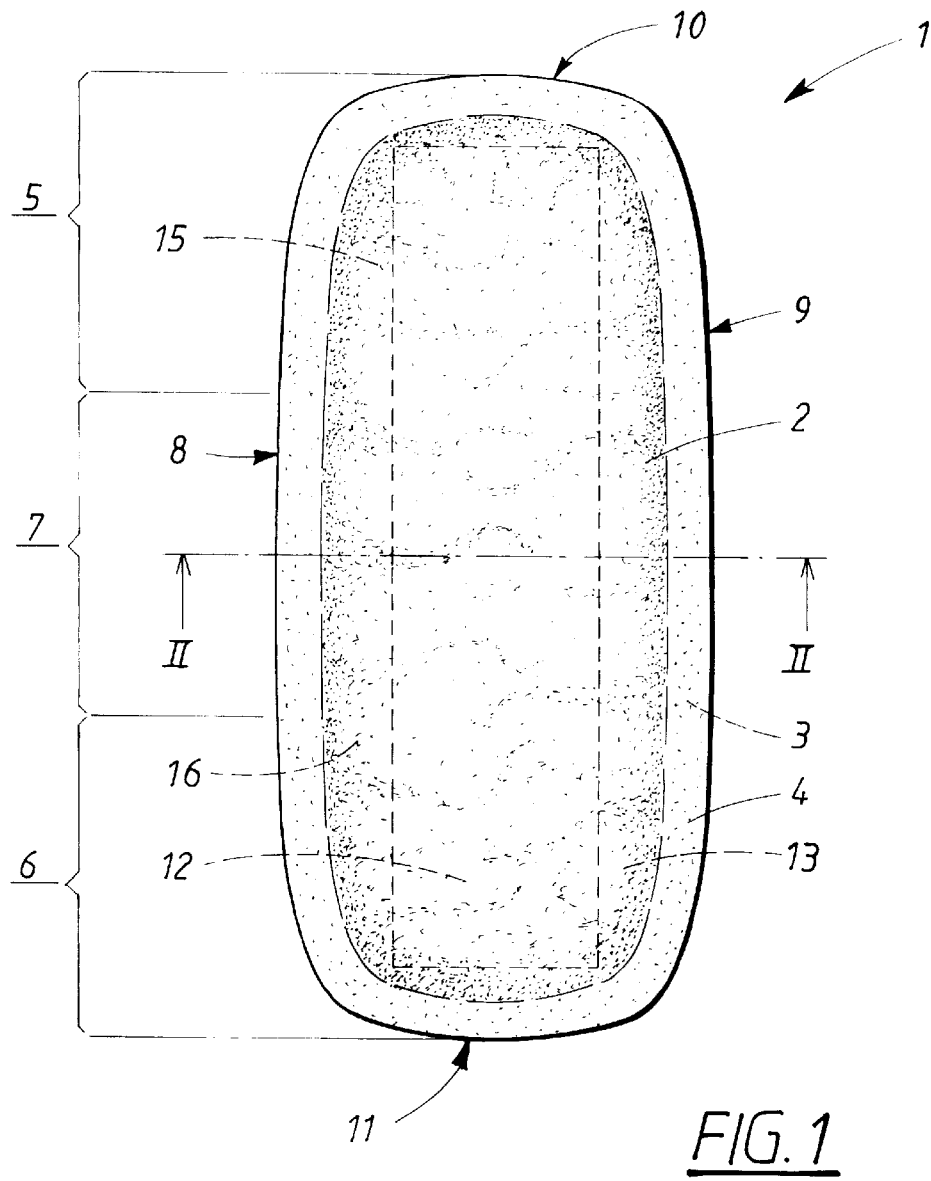
FIG. 1 shows a plan view of a sanitary napkin according to one embodiment of the invention seen from the surface which faces towards the user during use.
Figure 2:
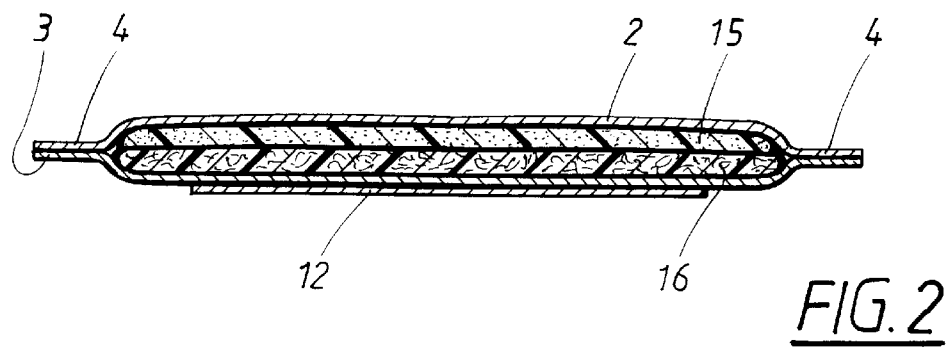
FIG. 2 shows a cross section along the line II—II through the sanitary napkin in FIG. 1.

The sanitary napkin shown in FIGS. 1–4 comprises a liquid-permeable cover layer 2, arranged over the surface of the sanitary napkin 1 which is intended to face towards a user during use. The liquid-permeable cover layer 2 preferably consists of a soft, skin-friendly material. Examples of liquid-permeable cover materials that can be used are various types of non-woven fabrics. Other liquid-permeable cover materials that exist are perforated plastic films, nets, knitted, crocheted or woven textiles and combinations and laminates of the listed material types.

The sanitary napkin 1 further comprises a liquid-impermeable cover layer 3, arranged on the side of the napkin 1, which is intended to face away from the user during use. A thin, flexible plastic film is usually used as a liquid-impermeable cover layer 3. However, it is also possible to use material layers which are initially liquid-permeable and which are coated with liquid-impermeable material. Other treatments, such as heat calendering to fuse an initially permeable material to a substantially liquid-impermeable layer, can also be used. Moreover, it is possible to use non-woven fabrics, or other textiles which are so compact and the fibres of which are so hydrophobic that they can function as a liquid-barrier layer.

The two cover layers 2, 3 are mutually joined and form a protruding joining edge 4 around the periphery of the napkin. The joining of the cover layers 2, 3 can be achieved using any known technique suitable for the purpose, such as gluing, welding or sewing.

The material of the liquid-permeable cover layer 2 is chosen so that it displays greater extensibility in the transverse direction of the sanitary napkin than the liquid-impermeable cover layer 3. The liquid-permeable cover layer 2 can be elastically extensible, which means that the layer 2 after stretching strives to return to a less stretched condition when the stretching force ceases. However, it is not necessary for the liquid-permeable cover layer 2 to be elastically extensible in the transverse direction. Accordingly, it is possible to use material that retains its stretched width even when the stretching force ceases. It is also possible to use a cover layer 2 which is pleated in the longitudinal direction of the sanitary napkin 1. When such a layer is stretched in the transverse direction of the napkin 1, the pleats are smoothed out completely or partially and the liquid-permeable cover layer assumes a greater width than before stretching.

Furthermore, the sanitary napkin 1 has an elongated, almost rectangular form and displays two end parts 5, 6 and an intermediate crotch part 7. The crotch part 7 is that part of the sanitary napkin 1 which is intended to be placed against the crotch of the user during use and to act as the main acquisition area for the body fluid which is secreted to the sanitary napkin 1. Moreover, the sanitary napkin displays two longitudinal side edges 8, 9 and two transverse end edges 10, 11.

An attachment member 12 in the form of a longitudinal rectangular area of self-adhesive glue is arranged on the surface of the liquid-impermeable cover layer 3 that faces away from the user. The attachment member 12 extends over the major part of the surface of the liquid-impermeable cover layer 3 between the two end edges 10, 11. The attachment member 12 is suitably covered before use by a removable protective layer, not shown in the figures, of paper, plastic film, or the like, which has been treated with a release agent. Naturally, it is possible to use other glue patterns than that shown here, such as longitudinal stripes, transverse areas, dots, circles, or other configurations. Neither is the invention limited to adhesive attachment members but, alternatively, friction attachment or different types of mechanical attachment devices, such as press studs, clips, girdles, pants or the like, can be used.

The sanitary napkin further comprises an absorbent body 13 for collecting body fluids. The absorbent body 13 is enclosed between the two cover layers 2, 3 and has, in the plane of the napkin, essentially the same general form as the napkin.

In the shown example, the absorbent body 13 comprises a first absorbent layer 15, which is arranged immediately inside the liquid-permeable cover layer 2, and a second absorbent layer 16, which is arranged between the first absorbent layer 15 and the liquid-impermeable layer 3.

The first absorbent layer 15 can consist of any material suitable for the purpose, but is preferably relatively soft and porous. For example, the absorbent body 15 can be a layer of fibrous wadding, cellulose fluff pulp, foam material, or the like. The first absorbent layer 15 is intended to be soft and comfortable against the body of the user. Moreover, the first absorbent body 15 should have good liquid-acquisition qualities, so that secreted body fluid can quickly be collected in the layer. The material in the first absorbent layer can comprise synthetic fibres or foam and can be completely or substantially non-absorbent in itself. In order to make such a material suitable for liquid-acquisition, it is suitable to treat the material so that it becomes more hydrophilic. This can be achieved, for example, by means of tensides.

It is advantageous if the first absorbent layer 15 has relatively high extensibility so that it can be stretched in the transverse direction when the sanitary napkin is deformed. Alternatively, the first absorbent layer 15 is free of attachments to other components in the napkin, whereby, when the napkin is curved, the layer 15 is free to move in relation to both the liquid-permeable cover layer 2 and the second absorbent layer 16.

The second absorbent layer 16 comprises a rigid material, for example a greatly compressed fibre layer. One type of material that has been found to be suitable for use in the second absorbent layer 16, is the absorbent material described in WO 94/10956. This material is a dry-formed fibre layer with high density and rigidity, which is used directly without previous defibration. Another similar material with qualities especially suited for blood absorption is described in WO 94/10953. The materials described in WO 94/10956 and WO 94/10953 both have relatively high rigidity. Moreover, these materials have very good absorption capacity.

Other materials which can fulfill the double function of constituting a second absorbent layer 16 in the sanitary napkin 1 and at the same time acting as a forming element for the sanitary napkin are rigid absorbent foam materials, greatly compressed layers of cellulose fluff pulp and rigid wadding materials, preferably with the addition of superabsorbent materials. Superabsorbent materials are polymers which can exist in the form of particles, flakes, fibres, film, or the like and which have the ability to absorb several times their own weight of body fluid by building a liquid-containing gel., In the embodiment shown in FIG. 3, the second absorbent layer 16 is attached to the liquid-impermeable cover layer 3, for example by gluing. The absorbent layer 16 can be attached to the liquid-impermeable cover layer 3 over the whole of the surface which lies against the cover layer 3. Alternatively, it is possible, however, to attach the absorbent layer 16 to the liquid-impermeable cover layer 3 only in individual points, stripes, or other patterns. Another alternative is to attach the absorbent layer 16 in the seal between the two cover layers 2, 3, as is shown in FIG. 4. Furthermore, the connection between the two layers 16, 3 can be limited to the crotch part of the sanitary napkin 7.

Figure 3:
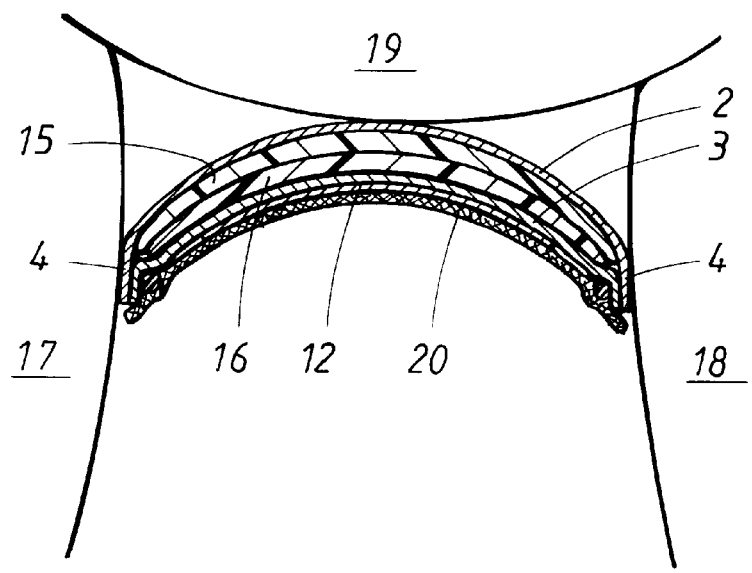
FIG. 3 shows a cross-section along the line II—II through the sanitary napkin in FIG. 1 as it appears during use.
Figure 4:
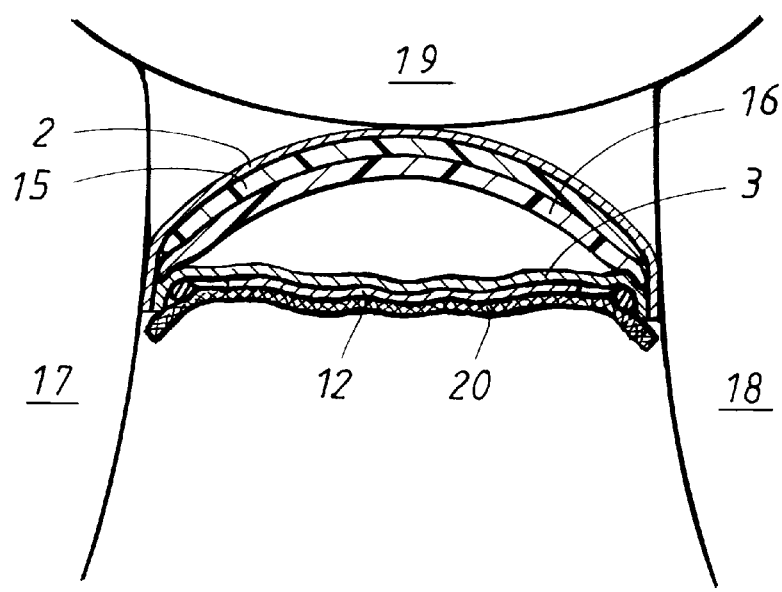
FIG. 4 shows an alternative cross-section along the line II—II through the sanitary napkin in FIG. 1 as it appears during use.

FIGS. 3 and 4 show two different versions of how the sanitary napkin 1 performs during use, depending on whether the second absorbent layer 16 is attached to the whole or a substantial part of the surface of the liquid-impermeable layer 3 or only along the side edges of the liquid-impermeable layer 3. The sanitary napkin is attached by means of the attachment member 12 inside the underpants 20 of the user. In FIG. 3, the material in the underpants is also curved when the sanitary napkin is compressed between the thighs 17, 18 of the user. In FIG. 4 only the absorbent body 13 of the sanitary napkin and the liquid-permeable cover layer 2 are curved, while the liquid-impermeable cover layer 3 with the attachment member 12 and the underpants 20 of the user are somewhat folded together between the side edges 8, 9 of the sanitary napkin.

During use, the sanitary napkin shown in FIG. 1 will, as mentioned, be compressed between the thighs 17, 18 of the user and, depending on the construction, will be deformed either as shown in FIG. 3 or as shown in FIG. 4. The deformation takes place by means of the absorbent body 13 being curved. As the liquid-permeable cover layer 2 is more extensible than the liquid-impermeable cover layer 3, the sanitary napkin will be forced to curve in the direction which offers least resistance. This means that the surface which lies against the crotch 19 of the user will assume a convex, curved form, such as is shown in FIGS. 3 and 4.

When the absorbent body 13 is curved, the liquid-permeable cover layer 2 is stretched out and adapts itself to the increased distance between the side edges 8, 9 of the surface of the sanitary napkin 1 that faces towards the user.

During use the liquid-impermeable cover layer 3 has substantially the same extension in the transverse direction of the sanitary napkin as when the napkin is in a plane condition. Preferably, the liquid-impermeable cover layer is substantially unresilient to the forces which arise when the second absorbent layer is curved, but if it is so desired the liquid-impermeable cover layer 3 can be of a material which allows limited stretching in the transverse direction. A liquid-impermeable cover layer 3 with a certain extensibility can facilitate the forming of a sanitary napkin in accordance with the embodiment shown in FIG. 3. As has already been pointed out however, in order for the curving of the sanitary napkin to occur in the correct direction, it is essential that the liquid-permeable cover layer 2 is more extensible than the liquid-impermeable cover layer 3.

The second absorbent layer 16 constitutes the forming element of the sanitary napkin. Thereby, the material in the absorbent layer 16 must be so rigid that it does not crease, break, fold or deform in any other uncontrollable way when the sanitary napkin 1 is compressed in the transverse direction. Instead, the compression results in the absorbent body 13 being curved to the arch shape shown in FIGS. 3 and 4. If the compression is great, it can occur, as shown in FIG. 4, that the liquid-impermeable cover layer 3 is folded or wrinkled somewhat to compensate for the reduced distance between the side edges 8, 9 of the sanitary napkin on the surface which faces away from the user.

Furthermore, it is suitable that the second absorbent layer 16 is not so rigid, or so hard that forces greater than those which normally arise during use of the sanitary napkin are necessary to deform the absorbent layer 16. A sanitary napkin with an absorbent layer that is too rigid or hard can cause discomfort in the form of pressure and chafing against the thighs 17, 18 of the user. The second absorbent layer 16 can advantageously consist of material with at least some resilience. Examples of such materials, which at least partly reassume their original form when the compression ceases, are elastically compressible foam materials and synthetic fibrous wadding.

Figure 5:
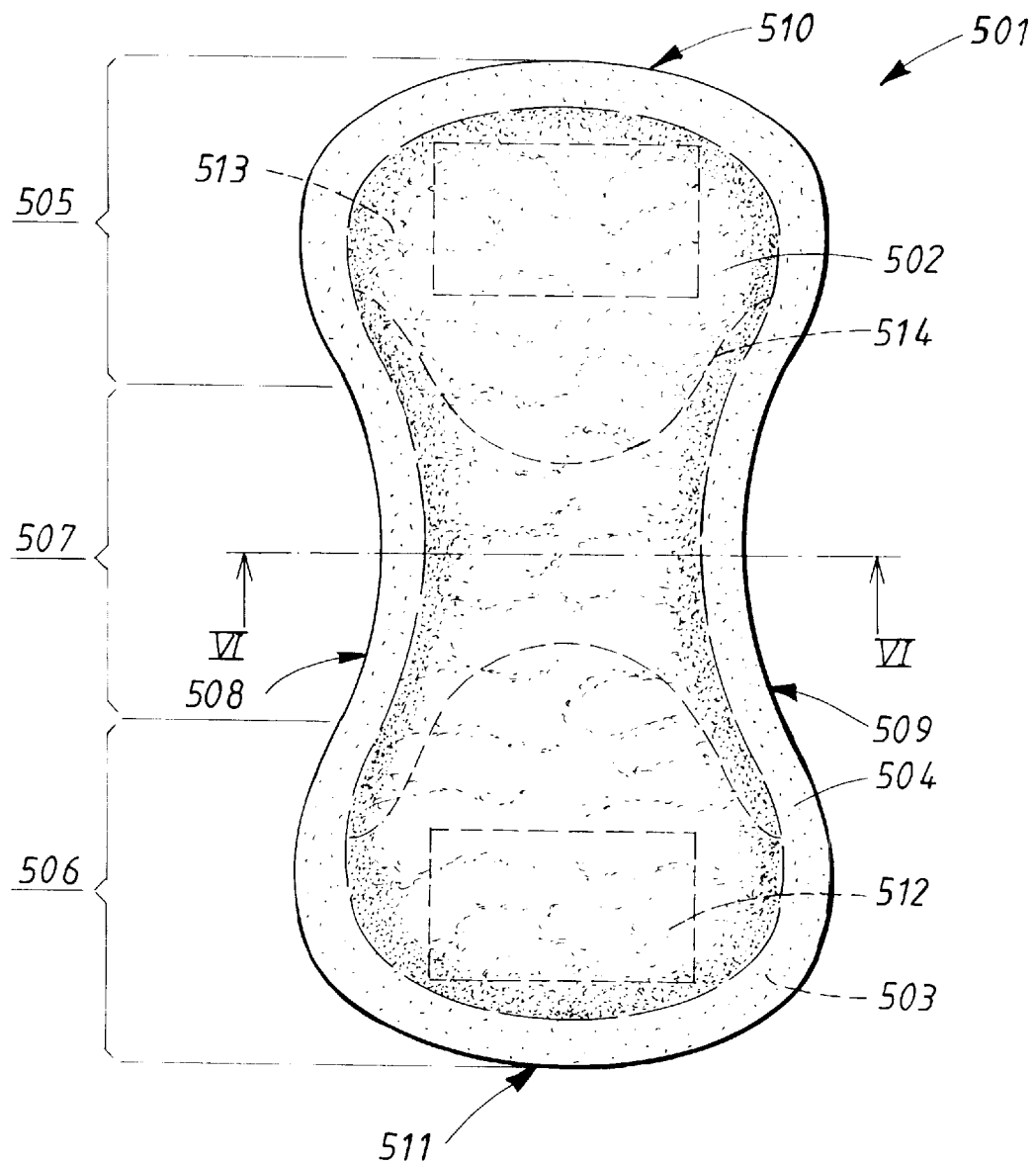
FIG. 5 shows a plan view of an incontinence protector in accordance with the invention seen from the side which faces towards the user during use.
Figure 6:
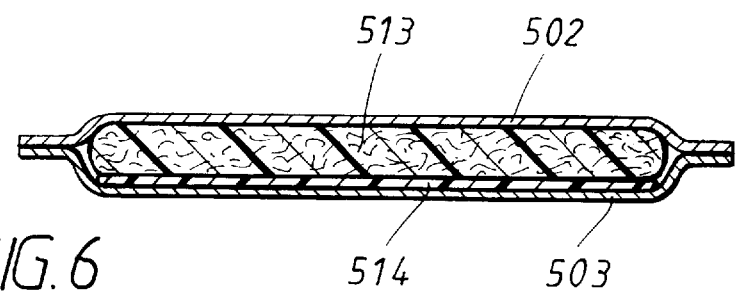
FIG. 6 shows a cross section along the line VI—VI through the incontinence protector in FIG. 4.
Figure 7:
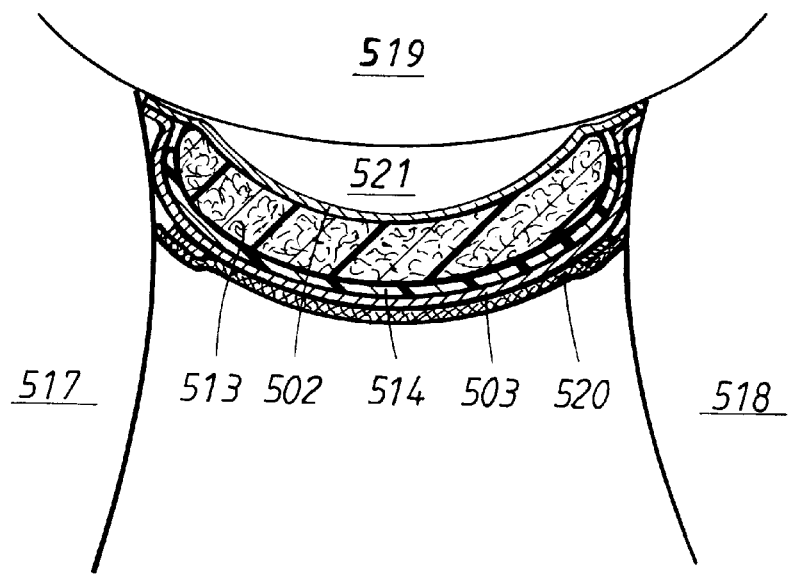
FIG. 7 shows a cross section along the line VI—VI through the incontinence protector in FIG. 4 as it appears during use.

The incontinence protector 501 shown in FIGS. 5–7 comprises a liquid-permeable cover layer 502, a liquid-impermeable cover layer 503 and an absorbent body 513 enclosed between the cover layers 502, 503. The liquid-permeable cover layer 502 is constituted, as in the previous embodiment, of a layer of non-woven material, perforated plastic film, net material, or the like. In a corresponding manner, the liquid-impermeable cover layer 503 can consist of a liquid-impermeable plastic film, a non-woven layer which has been coated with a liquid barrier material, or some other easily flexible material layer which has the ability to resist liquid penetration. The two cover layers 502, 503 have a somewhat greater extension in the plane than the absorbent body 513 and extend a certain distance out beyond the absorbent body 513 around the whole of its periphery. The cover layers 502, 503 are mutually joined within the projecting parts 504, for example by means of gluing or welding with heat or ultrasound.

The two cover layers 502, 503 are chosen so that the liquid-impermeable cover layer 503 has greater extensibility in the transverse direction of the incontinence protector than the liquid-permeable cover layer 502. Preferably, the liquid-permeable cover layer 502 is not extensible or is only extensible to an insignificant degree during the forces which arise during use of the incontinence protector.

The absorbent body 513 can be of any type suitable for the purpose. Examples of commonly occurring absorbent bodies are cellulose fluff pulp, tissue layers, highly absorbent polymers, absorbent foam materials, absorbent non-woven materials and the like. Material mixtures and absorbent bodies built up of layers of materials of different types and with different characteristics can also be used.

The incontinence protector 501 is substantially hour-glass-shaped, with broader end parts 505, 506 and a narrower crotch part 507 situated between the end parts 505, 506. The crotch part 507 is the part of the incontinence protector 501 that is intended to be situated in the crotch of the user during use and to act as an acquisition area for the body fluid that is secreted to the incontinence protector 501. Moreover, the incontinence protector 501 displays two longitudinal rounded side edges 508, 509 and two transverse curved end edges 510, 511.

On the outside of the liquid-impermeable cover layer 503 a self-adhesive attachment member 512 in the form of a transverse glue area is arranged at each end part 505, 506. In a corresponding manner to the sanitary napkin in FIGS. 1–4, other glue patterns and/or attachment members can of course be used.

An incontinence protector 501 of the type shown in FIGS. 5–7 is primarily intended to be used by persons with relatively mild incontinence problems and therefore has such a size that it can easily be accommodated inside a pair of normal underpants. The attachment member 512 serves to hold the incontinence protector in place inside the underpants during use.

The incontinence protector 501 further comprises a forming element 514 which advantageously is formed of plastic with a certain rigidity. Other suitable materials for the forming element are bound web with low bulkiness, foamed plastic or similar materials which give flexural resistance but are nevertheless sufficiently flexible to be able to be deformed by curving on compression with a force in the region of that which occurs during use of an absorbent article.

The forming element 514 is shown in FIG. 5 as an, in the plane, almost H-shaped insert. However, the invention shall not be considered to be limited to this form but also forming elements with the same form as the absorbent body 513, and also, for example, rectangular, stepped or oval forming elements are contemplated. The shown forming element 514 is attached to the absorbent body 513 as well as to the liquid-impermeable cover layer 503, for example by gluing or welding. However, it is conceivable to attach the forming element only to either one of these components.

When the incontinence protector is being used and is placed inside the underpants 520 of the user, it is compressed between the thighs 517, 518 of the user as is shown in FIG. 7. Thereby, the forming element 514 is curved. Since the liquid-impermeable cover layer 503 is more extensible than the liquid-permeable cover layer 502, the curving occurs in a direction away from the crotch 519 of the user, so that a bowl-shaped space 521 is formed between the crotch 519 and the incontinence protector. The bowl-shaped space 521 can collect relatively large amounts of liquid and retain the liquid until has gradually been absorbed into the absorbent body 513.

Figure 8:
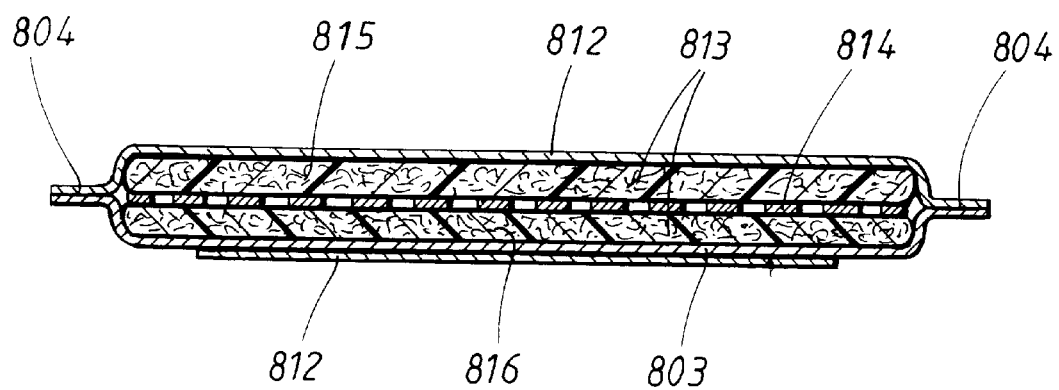
FIG. 8 shows a cross section through an absorbent article according to an alternative embodiment.

FIG. 8 shows a cross section through an absorbent article 801 according to a further embodiment of the invention. The absorbent article 801 comprises a liquid-permeable cover layer 802, a liquid-impermeable cover layer 803 and an absorbent body 813 enclosed between the two cover layers 802, 803. The absorbent body consists of a first absorbent layer 815 and a second absorbent layer 816. The absorbent layers 815, 816 can be of the same or different materials. The absorbent article is moreover provided with an adhesive attachment member 812 arranged on the liquid-impermeable cover layer 803.

Furthermore, a forming element 814 is arranged between the two absorbent layers 815, 816. The forming element is liquid-permeable and consists of, for example, a rigid plastic net, a perforated rigid plastic layer, or the like. The rigidity of the forming element 814 is such that compression of the article in the transverse direction during use causes the forming element to curve into an arch shape between the side of the article 808, 809. The direction of the curve can be controlled in accordance with the invention by choosing materials with different extensibility for the cover layers 802, 803. Accordingly, an absorbent article is obtained which, during use, assumes a bowl shape facing towards the user if the liquid-impermeable cover layer 803 is more extensible than the liquid-permeable cover layer 802. In a corresponding manner, a hump facing towards the user is formed if the liquid-permeable cover layer 802, is more extensible than the liquid-impermeable cover layer 803.

The liquid-permeable forming element 814 in FIG. 8 is attached to one or both of the absorbent layers 815, 816. Alternatively, it is conceivable to form the forming element 814 with a somewhat greater width than the absorbent body 813 so that the forming element 814 extends out into the edge seal 804 and is attached between the two cover layers 802, 803. However, this is a less preferred embodiment as there is a risk of the relatively rigid material in the forming element 814 chafing the skin of the user.

The invention should not be considered to be limited to the embodiments described herein, a number of further variations and modifications being possible within the scope of the following claims. Moreover, the different embodiments can be freely combined with one another, for example with regard to the form and location of the forming elements in the articles.

What is claimed is:

1. An absorbent article with a longitudinal direction and a transverse direction and displaying a crotch part and two end parts, and comprising:

a liquid-permeable cover layer intended to face towards a user during use;

a liquid-impermeable cover layer intended to face away from the user during use;

an absorbent body enclosed between the two cover layers;

said two cover layers having differing extensibility in the transverse direction of the article;

a forming element which is rigid in the transverse direction, and which extends in the transverse direction of the article at least in the crotch part; said forming element being permanently attached to at least one component in the article;

whereby compression of the article in the transverse direction will force the forming element to curve in a direction towards the cover layer displaying the greater extensibility in the transverse direction.

2. The absorbent article according to claim 1, wherein the liquid-permeable cover layer displays greater extensibility in the transverse direction of the article than the liquid-impermeable cover layer, whereby compression of the article in the transverse direction causes the forming element to curve in a direction towards the liquid-permeable cover layer whereby the article during use displays a raised portion facing towards the user.

3. The absorbent article according to claim 1, wherein the liquid-impermeable cover layer displays greater extensibility in the transverse direction of the article than the liquid-permeable cover layer, whereby compression of the article in the transverse direction causes the forming element to curve in a direction towards the liquid-impermeable cover layer whereby the article during use displays a bowl-shaped space facing towards the user.

4. The absorbent article according to claim 1, wherein the forming element comprises a fibre layer with a density in the range of 0.2–1.0 g/cm$^3$.

5. The absorbent article according to claim 1, wherein the forming element comprises a plastic layer.

6. The absorbent article according to claim 5, wherein the forming element comprises a foamed plastic layer.

7. The absorbent article according to claim 1, wherein the cover layer which displays the greater extensibility is elastically extensible.

8. The absorbent article according to claim 1, wherein the forming element is attached to the liquid-impermeable cover layer.

9. The absorbent article according to claim 1, wherein the forming element is attached to the liquid-permeable cover layer.

10. The absorbent article according to claim 1, wherein the forming element is attached to the absorbent body.

11. The absorbent article according to claim 1, wherein both cover layers extend beyond the absorbent body and are mutually attached in an edge seal, and the forming element is attached in the edge seal.

12. The absorbent article according to claim 1, wherein the forming element is liquid-permeable.

* * * * *